United States Patent
Coquet et al.

(10) Patent No.: US 11,083,686 B2
(45) Date of Patent: Aug. 10, 2021

(54) COSMETIC PREPARATION CONTAINING WHITE TRUFFLE EXTRACT AND COSMETIC METHOD THEREOF

(71) Applicant: ISP Investments LLC, Wilmington, DE (US)

(72) Inventors: Corinne Coquet, Cipieres (FR); Rachel Chabert, Grasse (FR)

(73) Assignee: ISP Investments LLC, Wilmington, DE (US)

( * ) Notice: Subject to any disclaimer, the term of this patent is extended or adjusted under 35 U.S.C. 154(b) by 0 days.

(21) Appl. No.: 16/604,465

(22) PCT Filed: Apr. 10, 2018

(86) PCT No.: PCT/EP2018/059190
§ 371 (c)(1),
(2) Date: Oct. 10, 2019

(87) PCT Pub. No.: WO2018/189194
PCT Pub. Date: Oct. 18, 2018

(65) Prior Publication Data
US 2020/0146971 A1    May 14, 2020

(30) Foreign Application Priority Data
Apr. 14, 2017   (CN) .......................... 201710244119.7

(51) Int. Cl.
| | | |
|---|---|---|
| *A61K 36/00* | (2006.01) | |
| *A61K 8/9728* | (2017.01) | |
| *A61Q 17/04* | (2006.01) | |
| *A61Q 19/08* | (2006.01) | |

(52) U.S. Cl.
CPC ............ *A61K 8/9728* (2017.08); *A61Q 17/04* (2013.01); *A61Q 19/08* (2013.01)

(58) Field of Classification Search
CPC ...................................................... A61K 36/00
USPC ......................................................... 424/725
See application file for complete search history.

(56) References Cited

U.S. PATENT DOCUMENTS 6,843,995 B2    1/2005   Golz-Berner et al.

FOREIGN PATENT DOCUMENTS

| CN | 104666237 A | 6/2015 |
|---|---|---|
| EP | 2599492 A1 | 6/2013 |
| WO | WO2016/007461 A1 | 1/2016 |

OTHER PUBLICATIONS

Age Defying Foundation SPF8, GNPD, MINTEL, (Mar. 2016), Database accession No. 3903005, XP002782516 [A] 1-16 * the whole document *.
"Lotion", GNPD, MINTEL, (Aug. 2012), Database accession No. 1866522, XP002782517 [A] 1-16 * the whole document *.
Database GNPD [Online] MINTEL; Oct. 2016 (Oct. 2016),"Cuticle Exfoliating Spray",Database accession No. 4356389.
References cited on the International Search report of PCT Application No. PCT/EP2018/059190 International Filing Date Apr. 10, 2018 and published under publication No. WO2018/189194 A4 dated Oct. 18, 2018.

*Primary Examiner* — Michael V Meller
(74) *Attorney, Agent, or Firm* — William J. Davis; Nathalie Tietcheu

(57) ABSTRACT

The present invention provides a process for obtaining an extract from White Truffle (*Tuber magnatum*) for skin cosmetic use, the white truffle extract obtainable by the process and a cosmetic composition comprising the said extract. The invention provides a method for reducing the signs of aging and lightening the skin.

1 Claim, 4 Drawing Sheets

COSMETIC PREPARATION CONTAINING WHITE TRUFFLE EXTRACT AND COSMETIC METHOD THEREOF

CROSS-REFERENCE TO RELATED APPLICATIONS

This application is a U.S. National Phase filing under 35 U.S.C. § 371 of International Application No. PCT/EP2018/059190, filed Apr. 10, 2018, and published as WO 2018/189194 A1 on Oct. 18, 2018, which claims benefit of priority Chinese Patent Application No. 20710244119.7 filed Apr. 14, 2017. The entire contents of each of the prior applications are incorporated herein by reference in their entirety.

TECHNICAL FIELD

The present invention is in the field of cosmetics and more specifically in the field of skin care. The invention relates to a process for preparing a white truffle (*Tuber magnatum*) extract by aqueous extraction, a white truffle extract obtainable by the process and a cosmetic composition comprising the white truffle extract.

The invention also relates to a method for reducing and/or correcting the signs of aging and photo aging of the skin, and to lighten the skin.

The white truffle extract can be used alone or in combination with other active agents.

BACKGROUND

The skin is a vital organ composed of several layers (dermis, proliferative layers and stratum corneum), which covers the entire surface of the body and ensures protective, sensitive, immune, metabolic or thermoregulatory functions. The skin, like the other organs, is subject to aging.

For example, the appearance of the skin is modified by various types of internal (disease and hormonal changes such as pregnancy) or external aggressions (environmental factors, such as pollution, sunlight, ultraviolet radiation, pathogens, etc.). Then wrinkles and fine lines, hyperpigmentation or hypopigmentation blemishes, dryness or even dehydration of the skin, thinning of the epidermis, elastosis, imperfections, age spots, etc., may appear.

In the skin, premature aging is observed, occurring in the areas exposed to ultraviolet radiation.

With age, skin appearance is altered. Dark spots, dull complexion, loss of tone uniformity are noticeable effect associated with age. The loss of skin youthful glow is often one of the first extrinsic signs of aging and constant exposure to the UV rays of the sun also causes the skin to appear dull and dry.

It is known that fungi are a wide family of living organisms. Fruiting bodies of some wild and cultivatable mushrooms contain medicinal compounds which are being used in traditional medicines and cosmetics. Fungi have developed during their evolution various properties to resist environmental stress and it is known that some fungi compounds can have an effect to moderate damages caused by life circumstance and natural environment on organisms. Thus, research for new natural bioactive compounds from fungi origin has intensified. For example, Inonotus obliquus mushroom contains enzyme such as Superoxide Dismutase (SOD), which is a key element in protecting the cell against ROS.

Also, truffles are known to be effective on certain conditions such as the improvement of immunity and hyperlipidemia. The genus *Tuber* belongs to Ascomycete phylum and is subterranean fungus. The *Tuber* fungi genus comprises some species of truffles. These truffle species are hypogenous fungi that establish an ectomycorrhizal symbiosis with trees and shrubs and form a fruiting body.

Some of the truffle species are highly priced as a food, due to their fruiting bodies characteristic aroma and delicious taste. These species are referred to by "truffles" or "real truffles" and they are precious and expensive delicacies which are widely used in the famous French and Italian cuisines.

Common truffles, which belong to the class of ascomycetes, order of Tuberales, have been appreciated as excellent edible fungi for many centuries and are of outstanding importance due to their special aroma. Truffles are underground fungi growing in symbiosis with oak tree roots and forming tuber-like fruiting bodies. In the extraction process of truffles, several active agents are set free. It has been found that a non-specific stimulation of the immune system can be achieved.

In the description of the invention "Truffles" refers to the following species: The Italian white truffles (scientific name: *Tuber magnatum* pico), the black truffle (also known as Perigord truffles from France, scientific name: *Tuber melanosporum*), the Burgundy truffle (*Tuber uncinatum*), Kalahari truffle (*Terfezia pfeilii*), Lion-Truffle (*Terfezia leonis*), summer truffle (*Tuber aestivum*), winter truffle (*Tuber brumale*), Chinese Truffle (*Tuber sinensis* or *Tuber indicum*) and Bianchetto or whitish truffle (*Tuber borchii*).

The white truffle (*Tuber magnatum*) is referred as Piedmont or Alba Truffle. Truffles grow a few inches down in the earth, in symbiosis with the roots of hardwood trees like oaks, chestnut, hazelnut and hornbeam. The irregularly shaped knobby little spheres range in size from around an inch and may weight over a pound (though truffles of that weight are rare). The firm flesh of a white truffle is pale cream to light brown in color, with white marbling throughout. Truffles are the true fruit of the earth, rarer and precious than any other edible root, tuber or mushroom. There is no other flavor like them on earth, which is perhaps why they are so often described as heavenly.

There have been many attempts to domestic these wild truffles, though they can take a decade to grow. Some of these attempts have been successful, but the most reliable source is still to forage for them in nature.

From the state of the art, numerous cosmetics are known which in some way contain plant-based raw materials in the form of oils or extracts. In most cases, the known advantageous effects of individual plants are used to achieve a corresponding overall effect.

The use of white truffle extract in a cosmetic composition is known in prior art. Most extract are total extracts or water-alcohol extracts. For example, the Chinese patent application, CN-A-104856928 disclosed an anti-wrinkle cosmetic wherein the active substance is one of mixture A, *Echinaceapurpurea extract*, and white truffle extract, or any combination thereof, and said mixture A is a mixture of trifluoroacetyl tripeptide-2, glycerol and dextran. U.S. Pat. No. 6,843,995 discloses a cosmetic preparation comprising of at least one aqueous extract of common truffles (Tuberacea) together with spray-dried champagne, wherein the active complex is provided in a cosmetic acceptable gel and stabilizer. Chinese patent CN-A-104666237 discloses a preparation method using hydro-alcoholic extract and the application of the truffle active ingredient for preparing an antioxidant and a skin whitening product. However, no document disclosed a water extracting method to prepare an entirely safe and effective cosmetic ingredient from white truffle.

Despite the various anti-aging cosmetic products on the market for the treatment of skin, there remains a need for effective topically applied cosmetic compositions that provide anti-aging or rejuvenating benefits to the skin, hair and/or nails using natural ingredients as active agent. Unnatural, chemically-synthesized products may be perceived as being environmentally or personally unsafe. In contrast, natural products are perceived as pure, mild, and superior to chemically synthesized products. Numerous natural based products extracted from plants or herbs are known to contain antioxidant/free-radical scavenging agents that can neutralize the effects of free-radical damage. Additionally, they can contain agents that stimulate the synthesis and restoration of damaged connective tissue structures in the dermis and barrier function in the epidermis.

There remains a need for cosmetic compositions which address the signs of aging, in particular the appearance of wrinkles, lines, and sagging. It is therefore an object of the present invention to provide new compositions and methods for treating, ameliorating, and/or preventing signs of aged or aging skin. It is a further object of the invention to improve the overall appearance of aging or aged skin.

The foregoing introduction is presented solely to provide a better understanding of the nature of the problems confronting the art and should not be construed in any way as an admission as to prior art nor should the citation of any reference herein be construed as an admission that such reference constitutes "prior art" to the instant application.

SUMMARY

The main aspect of the present invention provides a process for obtaining an extract containing fruiting body of a mushroom (White Truffles) of the genus *Tuber magnatum*, comprising the following steps:
   (i) adding water to white truffles to make a mixture,
   (ii) agitating the said mixture by maintaining temperature from RT (Room Temperature) to below 80° C.
   (iii) filtering the mixture to remove the solid f part to obtain the extract.

In another aspect, the present invention provides a white truffle extract obtained by the process of the present invention.

In another aspect, the present invention provides a cosmetic composition comprising white truffle extract obtained by aqueous extraction, wherein the white truffle extract comprises compounds having a molecular weight of less than 60 kDa in a physiologically acceptable medium.

In yet another aspect, the present invention provides a method for reducing and/or correcting the signs of aging and photo-aging of the skin, comprising topically applying to the skin a cosmetic composition comprising white truffle extract obtained by aqueous extraction, wherein the white truffle extract comprises compounds having a molecular weight of less than 60 kDa in a physiologically acceptable medium.

In yet another aspect, the present invention provides a method for reducing skin pigmentation and/or lightening the skin, comprising topically applying to the skin a cosmetic composition comprising white truffle extract obtained by aqueous extraction, wherein the white truffle extract comprises compounds having a molecular weight of less than 60 kDa in a physiologically acceptable medium.

BRIEF DESCRIPTION OF THE DRAWINGS

Further embodiments of the present invention can be understood with the appended figures.

DETAILED DESCRIPTION

Figure 1:
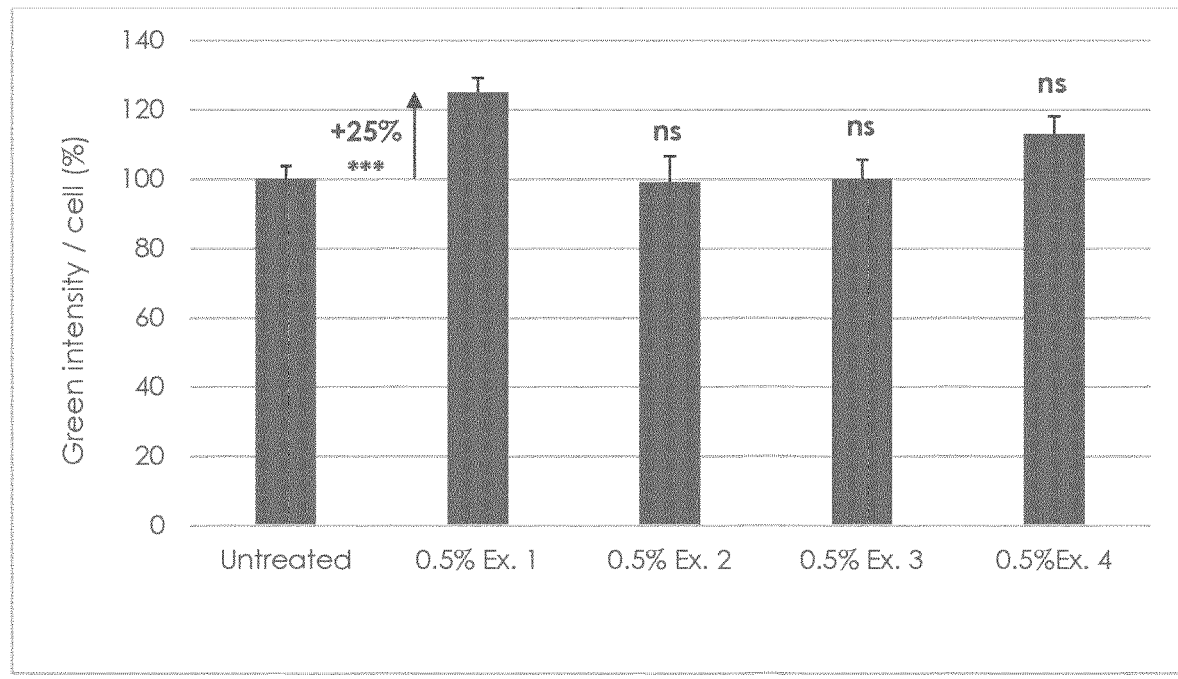
FIG. 1 is illustration of collagen I expression on fibroblasts assessed by immunofluorescence.

Detailed embodiments of the present invention are disclosed herein; however, it is to be understood that the disclosed embodiments are merely illustrative of the invention that may be embodied in various forms. Therefore, specific structural and functional details disclosed herein are not to be interpreted as limiting, but merely as a representative basis for teaching one skilled in the art to variously employ the present invention.

Whenever a term is identified by reference to a range, the range will be understood to explicitly disclose every element thereof. As a non-limiting example, a range of 1-10% will be understood to include 1%, 2%, 3%, 4%, 5%, 6%, 7%, 8%, 9%, and 10%, and all values between 1 and 10%.

Where two or more substituents are referred to as being "selected from" a group of enumerated alternatives, it is meant that each substituent can be any element of that group, independent of the identity of the other substituents.

As used herein, "%" refers % by weight, that is the weight percent of a component in relation to the total weight of the composition (i.e., including any carriers, vehicles, solvents, fillers, or other components added before application to the skin) unless otherwise provided.

All terms used herein are intended to have their ordinary meaning unless otherwise provided. For the purposes of describing and claiming the present invention, the following terms are defined:

"Extract" is understood to be any substance or isolated preparation extracted from a natural source, regardless of extraction method or ingredients. The term is used in a broad sense including, for example, ingredients soluble in water or an organic solvent extracted from a natural substance using the solvent, or specific ingredients of a natural substance.

"Aqueous extract" is understood to be a mixture of compounds obtained by extraction with water.

It is understood by "physiologically acceptable" that the white truffle extract according to the invention, or a composition containing said agent, is suitable for coming into contact with the skin or a mucus membrane without provoking a toxicity or intolerance reaction.

"Cutaneous signs of aging and photo-aging" refers to all changes in the external appearance of the skin and keratinous appendages due to aging, such as, for example, thinning of the skin, sagging, loss of hydration and atonia, deep wrinkles and fine lines, loss of firmness, dullness, dermal atrophy or any other internal degradation of the skin resulting from exposure to ultraviolet radiation such as age spots.

"skin lightening" refers to the improvement in skin tone, radiance, and/or clarity and/or restoration of skin luster or brightness.

The species name "*Tuber magnatum*", or "white truffle" or "trifola d'Alba Madonna" ("Truffle of the White Mother" in Italian) is found mainly in the Langhe and Montferrat areas of the Piedmont region in northern Italy and, most famously, in the countryside around the cities of Alba and Asti. White truffle is characterized by a specific smell very fine and rare, 81% humidity, protein content around 10% and sugar content around 2%.

As used herein, "skin" refers to all of the covering tissue constituting the skin, the mucous membranes and the keratinous appendages, including hair, nails, eyelashes and eyebrows.

"Topical application" is understood to be the application or spreading of a composition containing said white truffle extract, on the surface of the skin or a mucus membrane.

What is described herein is a process for obtaining an extract from grounded white truffle, cosmetic composition comprising the extract, method of reducing and/or correcting the signs of aging and photo-aging of the skin by topically applying the composition comprising white truffle extract to the skin.

Antioxidants play an important role as health protecting factors. Scientific evidence suggests that antioxidants reduce the risk for chronic diseases including cancer and heart disease. Primary sources of naturally occurring antioxidants are whole grains, fruits, flower and vegetables. Plant antioxidants are vitamin C, vitamin E, carotenes, phenolic acid, flavonoids.

The white truffle extract according to the invention is known to be rich in polyphenolic compounds, such as phenolic acids. All these water-soluble molecules known for their antioxidant activity contribute to provide the antioxidant potent of the white truffle extract according to the invention. Total polyphenols content measured is 100 mg/kg of the extract.

Polyphenolic compounds are recognized to be powerful antioxidant molecules. "Polyphenolic compounds" are compounds found abundantly in natural plant food sources that have antioxidant properties. They refer to all the classes of polyphenols, they mean compounds comprising at least one diphenol aromatic ring, phenol group may be optionally etherified or esterified. They can also be called simply "polyphenol".

Polyphenols play an important role in maintaining your health and wellness. Antioxidants as a group help protect the cells in your body from free radical damage, thereby controlling the rate at which you age. Antioxidants can be divided into three major groups: Carotenoids, Allyl sulfides, found in garlic and onions, Polyphenols (also known as phenolics).

Polyphenols can be further broken down into four categories: phenolic acids, flavonoids, lignans, and stilbenes, with additional subgroupings based on the number of phenol rings they contain, and on the basis of structural elements that bind these rings to one another.

Phenolic acid is a type of phytochemical called polyphenol, found in a variety of plant based foods; the seeds and skins of fruits and the leaves of vegetables contain the highest concentrations. Phenolic acids are readily absorbed through the walls of the intestinal tract, and they may be beneficial to health because they work as antioxidants that prevent cellular damage due to free-radical oxidation reactions. There are many different phenolic acids found in nature, and they can be divided into two categories: benzoic acid derivatives, such as gallic acid; and cinnamic acid derivatives, including caffeic acid and ferulic acid. The cinnamic acids are more common than the benzoic acids.

In the present invention "white truffle extract" means the extract is obtained from the fresh or freezed grounded fruiting body of the mushroom *Tuber magnatum*.

The white truffle extract according to the invention can be obtained by aqueous extraction. A large number of compounds found in white truffle extract are likely to have biological activity are water soluble.

In a preferred embodiment, the present invention provides a process for obtaining an extract from white truffle (*Tuber magnatum*), said process comprising:
 (i) adding water to grounded white truffle to make a mixture,
 (ii) agitating the said mixture for 2 hours by maintaining temperature from RT to below 80° C.
 (iii) filtering the mixture to remove the solid part to obtain the extract.

In a preferred embodiment the grounded white truffle is macerated in water. The solution is subjected to short time gentle maceration for 2 hours at a temperature between RT to less than 80° C. Most preferably the temperature is maintained between RT to 50° C. to preserve the integrity of molecules of interest such phenolic acids and so their ability to act as antioxidant.

The selection of the extraction temperature depends on the desired type of compounds to be extracted, the structural characteristics of the botanical source (flowers, fruits, stems, seeds, leaves, root), the quality and yield required for the extract, and the economic feasibility for scaling up the process. The extraction of the phenolic compounds from the plant material is influenced by the extraction temperature and time, which reflects the conflicting actions of solubilization and analyte degradation by oxidation. However, many phenolic compounds are easily hydrolyzed and oxidized. Long extraction times and high temperature increase the chance of oxidation of phenolics which decrease the yield of phenolics in the extracts. The analysis was done at different temperatures and showed that high temperatures degrade these types of molecules.

The water extraction can be carried out at room temperature or with water heated at no more than 80° C., while being agitated. Several processes of extraction were tested and selected as preserving the integrity of molecules present in truffles, with an acceptable yield while removing the volatile flavoured molecules responsible for characteristic truffle odor. The targeted molecules being fragile, it had been shown that the extraction at 50° C. best met the needs of the invention. Thus preferably, the extraction is carried out by maceration in water heated at 50° C. for 2 hours. The raw solution is then subjected to grid filtering to remove insoluble material. After grid filtering, the aqueous or liquid fraction is collected. To remove smaller residues of the aqueous extract, a filtration by any process well known by someone skilled in the art may be carried out.

In a preferred embodiment, the purification process begins by successive filtrations using filters with decreasing porosity from about 50 to about 20 µm until about 0.5-0.2 µm to get an extract. Preferably, the filters have a decreasing porosity of 50 to 20 µm until t 0.5 µm to 0.2 µm.

In a preferred embodiment, the purification process is followed by a double purification by activated carbone.

In another preferred embodiment, the extract obtained is composed of protein fragments and peptides with a molecular weight of less than 60 kDa, as demonstrated by sodium dodecyl sulfate polyacrylamide gel electrophoresis (SDS-PAGE). The obtained extract is a clear and brilliant solution.

In another preferred embodiment, the extract is then diluted at a concentration between 0.5 g/Kg and 1.5 g/Kg, preferably at 1 g/Kg of dry matter with solvents, such as water, glycerol, ethanol, propanediol, butylene glycol, dipropylene glycol, ethoxylated or propoxylated glycols, cyclic polyols or any mixture of these solvents for example 30% butylene glycol and 2% of 1.2 hexanediol by maintaining the pH between 4 to 5.

Then, the diluted white truffle extract is sterilized by sterile filtration. Then the solution is heated overnight at 65° C. to perform low-temperature pasteurization.

Furthermore, the diluted white truffle extract diluted at a concentration between 0.5 g/Kg and 1.5 g/Kg, of dry matter with solvents can be qualitatively and quantitatively analyzed. The characteristics are the following:

Proteins: 0.05-0.15 g/kg,
Sugars: 0.35-1.05 g/kg,
Amino acids: 0.025-0.075 g/kg,
Phenolic compounds: 0.05-0.15 g/kg,
The extract does not contain any ceramide or sphingolipid.

Protein contents of the white truffle extract have been determined by Lowry protein assay (Lowry O H, Rosebrough N J, Farr A L, Randall R J (1951). "Protein measurement with the Folin phenol reagent", J. Biol. Chem. 193 (1): 265-75) which has been used to quantify total protein content of the extract. The Lowry assay is a biochemical assay for determining the total level of protein in a solution. The Lowry method is based on the reaction of Cu+, produced by the oxidation of peptide bonds, with Folin-Ciocalteu reagent. The absorbance of the sample is read on the spectrophotometer at 550 nm. The protein content is determined using a BSA standard curve.

Aminoacid content of the white truffle extract have been determined starting from a protocol published by Moore et al. (Moore et al, "Photometric ninhydrin method for use in the chromatography of amino acids", Journal of Biological Chemistry 1948 Vol. 176 pp. 367-388). The free amino acid content of the extract was assessed by the formation of a colored complex, following the rupture of the amine and carboxylic functions by the reagent ninhydrin. The absorbance of the complex is read on the spectrophotometer at 570 nm. The total amino acids content is determined using a standard curve of amino acids pool.

Total sugars content in the white truffle extract was determined by colorimetry via an adaptation of the assay described by (Dubois et al. ("Colorimetric Method for Determination of Sugars and Related Substances", Anal. Chem., 1956, 28 (3), 350-356). This analysis consists in the dissolution of the raw material in concentrated sulfuric acid and then reacting with phenol to form a colored complex. The absorbance of the complex is read on the spectrophotometer at 490 nm. The sugar content is determined using a glucose standard curve.

Polyphenols content of the white truffle extract was determined using the Folin-Ciocalteu assay (Singleton et al. (1999). "Analysis of total phenols and other oxidation substrates and antioxidants by means of Folin-Ciocalteu reagent", 299: 152). Polyphenols compounds in the sample react with the Folin-Ciocalteu reagent, the oxidation of the reagent give a blue color. The absorbance of the sample is read on the spectrophotometer at 760 nm. The content was expressed as gallic acid equivalents using a gallic acid standard curve.

SDS-PAGE electrophoresis was performed to assess molecular weight of proteins of the extract. The white truffle extract is heated to 70° C. for 10 minutes in reductive denaturing conditions in a denaturing sample buffer. An antioxidant solution is added to the inner chamber (cathode) so that the reduced proteins do not re-oxidize during electrophoresis. Protein migration is carried out using the MES running buffer with standard Novex® Sharp as a marker for molecular weight. Protein staining is carried out using silver staining.

The present application provides a cosmetic composition comprising white truffle extract obtained by aqueous extraction, wherein the white truffle extract comprises compounds having a molecular weight of less than 60 kDa and a physiologically acceptable medium.

The advantage of the extract according to the invention is that small compounds are more stable and reproducible without having an allergenic effect.

In another preferred embodiment, the white truffle extract is present in a concentration range from about 0.01% to about 20% by weight, preferably 0.1% to about 5% by weight of the total weight of the composition.

In another embodiment, the white truffle extract is used for cosmetic applications, more preferably for topical applications.

In another preferred embodiment, the present invention provides oral, parenteral or topical formulations adapted by the person skilled in the art, in particular for cosmetic or dermatological compositions. The compositions according to the invention are advantageously designed to be administered topically. These compositions must therefore contain a physiologically acceptable medium, i.e. compatible with the skin, and cover all cosmetic or dermatological forms.

Further, the present compositions preferably are in the form of an aqueous, hydroalcoholic or oily solution; oil-in-water emulsion, water-in-oil emulsion or multiple emulsions; creams, suspensions, powders adapted for application on the skin, mucus membranes, lips and/or keratinous appendages. These compositions can also be more or less fluid and have the appearance of a cream, a lotion, milk, a serum, pomade, a gel, a paste or a mousse. They can also exist in solid form, as a stick, or can be applied to the skin as an aerosol. They can also be used as a skincare product and/or as a makeup product.

In another embodiment, the composition comprises conventionally used additive envisaged in the scope of application as well as necessary additives for their formulation, such as co-solvents (ethanol, glycerol, benzyl alcohol, damper . . . ), thickeners, thinners, emulsifiers, antioxidants, colorants, solar filters, pigments, fillers, preservatives, perfumes, odor absorbers, essential oils, oligo elements, essential fatty acids, surfactants, film-forming polymers, chemical filters or minerals, moisturizing agents or thermal waters etc. Water-soluble, preferably natural, polymers, such as polysaccharides or polypeptides, cellulose derivatives of the type methylcellulose or hydroxypropylcellulose, or even synthetic polymers, poloxamers, carbomers, siloxanes, PVA or PVP, and in particular polymers sold by the company Ashland, can be cited, for example.

It is well understood that the white truffle extract according to the invention can be used on its own or in conjunction with other active ingredients.

Furthermore, the compositions which can be used according to the invention advantageously contain at least one other active agent. The following types of ingredients can be cited, in a non-limiting manner: other peptide active agents, vegetable extracts, healing agents, anti-aging agents, anti-wrinkle agents, soothing agents, anti-free radicals, anti-ultraviolet radiation agents, agents for stimulating dermal macromolecular synthesis or energetic metabolism, moisturizing agents, antibacterial agents, antifungal agents, anti-inflammatories, anesthetics, agents modulating cutaneous differentiation, cutaneous pigmentation or depigmentation, and agents for stimulating nail and hair growth.

In a more specific embodiment, the composition according to the invention will comprise:

Sunscreens, ultraviolet and Infra-red screens

Anti-free radical agents,

DHEA (dehydroepiandrosterone),

At least one cytochrome co-activating compound, and/or;

One (or more) aquaporin-activating compound and/or;

One (or more) sirtuin-activating compound and/or;

One (or more) compound that increases cell adhesion and/or;

One (or more) compound that increases the production of matrix proteins of the collagen or laminin type, etc.;

One (or more) HSP protein-modulating compound;

One (or more) compound that increases cell energy;

One (or more) pigmentation-modulating compound such as a yeast, amaranth, linseed, bean, cacao, corn, soy, sunflower, rapeseed or pea peptide extract;

One (or more) compound improving the skin barrier function;

One (or more) mitochondria-protecting compound.

Vitamin A and notably retinoic acid, retinol, retinol propionate, retinol palmitate, Vitamin B3 and notably niacinamide, nicotinate of tocopherol, Vitamin B5, vitamin B6, vitamin B12, panthenol, Vitamin C, and notably ascorbic acid, ascorbyl glucoside, ascorbyl tetrapalmitate, magnesium and sodium ascorbyl phosphate, Vitamins E, F, H, K, PP, and coenzyme Q10, Metalloproteinase inhibitor, activator of Tissue Inhibitor Metalloproteinase (TIMP), Aminoacids and notably arginine, ornithine, hydroxyproline, hydroxyproline dipalmitate, palmitoylglycine, hydroxylysine, methionine and its derivatives, N-acylated aminoacids, Natural or synthetic peptides, including, di-, tri-, tetra-, penta- and hexapeptides and their lipophilic derivatives, isomers and complex with other molecules such as metallic ion (i.e. copper, zinc, manganese, magnesium, and others), peptides sold under commercial names MATRIXYL®, ARGIRELINE®, CHRONOGEN™, LAMINIXYL IS™, PEPTIDE Q10™, COLLAXYL™ (patent FR2827170, ASHLAND®), PEPTIDE VINCI 01™ (patent FR2837098, ASHLAND®), PEPTIDE VINCI 02™ (patent FR2841781, ASHLAND®), ATPeptide™ (patent FR2846883, ASHLAND®) or synthetic peptide of sequence Arg-Gly-Ser-NH2, sold under commercial name of ATPeptide™ by ASHLAND®;

Extract of *Artemia salina*, sold under commercial name of GP4G™ (FR2817748, ASHLAND®);

Botanical peptide extracts such as flaxseed extract (Lipigenine™, patent FR2956818, ASHLAND®), soya extract, einkorn, grapevine, rapeseed, rice, corn or pea;

Yeast extracts, such as Dynagen™, (patent FR2951946, ASHLAND®) or Actopontine™ (patent FR2944526, ASHLAND®); dehydroacetic acid (DHA), Natural or synthetic phystosterols, alpha- and beta-hydroxyacids, silanols, Sugar amines, glucosamine, D-glucosamine, N-acetyl-glucosamine, N-acetyl-D-glucosamine, mannosamine, N-acetyl mannosamine, galactosamine, N-acetyl galactosamine, Polyphenols, isoflavones, flavonoids, such as grape extract, pine extract, olive extract, Lipids such as ceramides or phospholipids, Animal oils such as squalenes or squalanes, Vegetal oils, such as almond oil, coconut oil, castor oil, jojoba oil, olive oil, rapeseed oil, peanut oil, sunflower oil, wheat germ oil, corn germ oil, soybean oil, cotton oil, alfalfa oil, poppy oil, pumpkin seed oil, evening primrose oil, millet oil, barley oil, rye oil, safflower oil, passion oil, hazelnut oil, palm oil, apricot kernel oil, avocado oil, calendula oil, ethoxylated vegetable oils, or shea butter, the above mentioned compounds can be natural, such as peptide hydrolysates of plants, or also synthetic, such as peptide compounds.

It is clear that the invention is designed for mammals in general, and more specifically for human beings. The inventors have indeed identified biological activities which are useful to reduce and/or correct the cutaneous signs of aging and photo-aging of the skin and to lighten the skin.

In yet another embodiment, the present application provides a cosmetic method for reducing and/or correcting the signs of aging and photo-aging of the skin, comprising topically applying to the skin, a composition comprising a white truffle extract according to the application. Preferably this cosmetic method comprises applying to the skin, a composition comprising a white truffle extract wherein the compounds have a molecular weight of less than 60 kDa in a physiologically acceptable medium.

In yet another aspect, the present application provides a cosmetic method to lighten the skin, wherein a cosmetic composition comprising a white truffle extract according to the invention is applied topically on the skin which is to be treated. Preferably this cosmetic method comprises applying to the skin, a composition comprising a white truffle extract wherein the compounds have a molecular weight of less than 60 kDa in a physiologically acceptable medium.

The embodiments which are specific to this cosmetic method also result from the above description.

Further advantages and characteristics of the invention can be seen in greater detail by reading the illustrative, non-limiting examples provided.

Example 1: Preparation of a White Truffle Extract (*Tuber magnatum*)

The white truffles (fruiting body) are obtained from Alba in Italy. The truffle 50 g of grounded freezed white truffle is placed in 1 liter of distilled water. The solution is heated 2 hours at temperature of 50° C. Then a filtration 20-50 µm is carried out to separate solid truffle residue from the liquid part is carried out. The purification process begins by successive filtrations using filters with decreasing porosity from 50-20 µm until 0.3-0.5 µm then 0.25% of activated carbon (Cabot Norit SXplus) is added to the solution and mixed during 30 minutes at 50° C.; the charcoal is then removed with a 0.3-0.5 µm filtration; another 0.25% of activated carbon (Cabot Norit SXplus) is added to the solution and mixed during 30 minutes at 50° C.; the charcoal is then removed with a 0.3-0.5 µm filtration. The filtrate is then diluted to obtain an extract having between 0.5-1.5 g/Kg dry matter with 30% butylene glycol and 2% hexanediol.

The pH of the solution is adjusted between 4 and 5 to increase the stability of the extract. After clarification and dilution, the filtrate is then filter-sterilized with 0.2 µm filter porosity under sterile condition. White truffle extract was analyzed using standard procedure. The characteristics of the white truffle extract obtained are the following: dry matter: 1 g/kg—proteins: 0.1 g/kg—sugars: 0.70 g/kg—amino acids: 0.01 g/kg and polyphenolic compounds 0.1 g/Kg.

Proteins content of the white truffle extract have been determined by Lowry protein assay (Lowry et al, 1951) to quantify total protein content of the extract. The Lowry assay is a biochemical assay for determining the total level of protein in a solution. The Lowry method is based on the reaction of Cu+, produced by the oxidation of peptide bonds, with Folin-Ciocalteu reagent. The absorbance of the sample is read on the spectrophotometer at 550 nm. The protein content was determined using a BSA (Bovine Serum albumin) standard curve. Aminoacid content of the extract have been determined starting from a protocol published by Moore et al (1948), the free amino acid content of the extract was assessed by the formation of a colored complex, following the rupture of the amine and carboxylic functions by the reagent ninhydrin. The absorbance of the complex is read on the spectrophotometer at 570 nm. The total amino acids content was determined using a standard curve of amino acids pool.

Total sugar content on the extract was determined colorimetrically via an adaptation of the assay described by Dubois et al (1956) (Dubois et al, "Colorimetric Method for Determination of Sugars and Related Substances", Anal. Chem., 1956, 28 (3), 350-356). This analysis consists in the dissolution of the raw material in concentrated sulfuric acid and then reacting with phenol to form a colored complex. The absorbance of the complex is read on the spectrophotometer at 490 nm. The sugar content is determined using a glucose standard curve.

Polyphenol content of the white truffle extract was determined using the Folin-Ciocalteu assay (Singleton et al., "Analysis of total phenols and other oxidation substrates and antioxidants by means of folin-ciocalteu reagent", 1999, 299: 152). Polyphenol compounds in the sample react with the Folin-Ciocalteu reagent, the oxidation of the reagent gives a blue color. The absorbance of the sample is read on the spectrophotometer at 760 nm. The content was expressed as gallic acid equivalents using a gallic acid standard curve SDS PAGE electrophoresis was performed to assess molecular weight of proteins of the extract. The white truffle extract is heated to 70° C. for 10 minutes in reductive denaturing conditions in a denaturing sample buffer. An Antioxidant solution is added to the inner chamber (cathode) so that the reduced proteins do not re-oxidize during electrophoresis. Protein migration is carried out using the MES running buffer with standard Novex® Sharp as a marker for molecular weight. Protein staining is carried out using silver staining.

The extract obtained is composed of peptides with a molecular weight of less than 60 kDa.

Example 2: Preparation of a White Truffle Extract (*Tuber magnatum*)

Briefly, the white truffles (fruiting body) are obtained from Alba in Italy. 100 g of freezed grounded white truffle is placed in 1 liter of distillated water. Solution pH is adjusted to 2 with chlorhydric acid. The solution is heated 2 hours at temperature of 80° C. Then a filtration 20-50 is carried out to separate solid truffle residue from the liquid part. The purification process begins by successive filtrations using filters with decreasing porosity from 50-20 µm until 0.3-0.5 µm then 1% of activated carbon (Cabot Norit SXplus) is added to the solution and mixed during 30 minutes at 50° C.; the charcoal is then removed with a 0.3-0.5 µm filtration. The filtrate obtained is 20 g/Kg dry matter and is then diluted to obtain an extract having between 0.5-1.5 g/Kg dry matter. The pH of the solution is adjusted between 4 and 5 to increase the stability of the extract. After clarification and dilution, the filtrate is then filter-sterilized with 0.2 µm filter porosity under sterile condition.

Example 3: Preparation of a White Truffle Extract (*Tuber magnatum*)

Briefly, the white truffles (fruiting body) are obtained from Alba in Italy. 100 g of freezed grounded white truffle is placed in 1 liter of distillated water. Solution pH is adjusted to 2 with chlorhydric acid. The solution is heated 2 hours at temperature of 80° C. Then a filtration 20-50 µm is carried out to separate solid truffle residue from the liquid part. The purification process begins by successive filtrations using filters with decreasing porosity from 50-20 µm until 0.3-0.5 µm then 0.25% of activated carbon (Cabot Norit SXplus) is added to the solution and mixed during 30 minutes at 50° C.; the charcoal is then removed with a 0.3-0.5 µm filtration; another 0.25% of activated carbon (Cabot Norit SXplus) is added to the solution and mixed during 30 minutes at 50° C.; the charcoal is then removed with a 0.3-0.5 µm filtration. The filtrate obtained is 20 g/kg dry matter and is then diluted to obtain an extract having between 0.5-1.5 g/Kg dry matter. The pH of the solution is adjusted between 4 and 5 to increase the stability of the extract. After clarification and dilution, the filtrate is then filter-sterilized with 0.2 µm filter porosity under sterile condition.

Example 4: Preparation of a White Truffle Extract (*Tuber magnatum*)

Briefly, the white truffles (fruiting body) are obtained from Alba in Italy. 100 g of freezed grounded white truffle is placed in 1 liter of a solution composed of 10 mM tetrasodic EDTA. The solution is heated 2 hours at temperature of 50° C. Then a filtration 20-50 µm is carried out to separate solid truffle residue from the liquid part. The purification process begins by successive filtrations using filters with decreasing porosity from 50-20 µm until 0.3-0.5 µm, then 0.25% of activated carbon (Cabot Norit SXplus) is added to the solution and mixed during 30 minutes at 50° C.; the charcoal is then removed with a 0.3-0.5 µm filtration; another 0.25% of activated carbon (Cabot Norit SXplus) is added to the solution and mixed during 30 minutes at 50° C.; the charcoal is then removed with a 0.3-0.5 µm filtration. The filtrate obtained is 20 g/kg dry matter and is then diluted to obtain an extract having between 0.5-1.5 g/Kg dry matter. The pH of the solution is adjusted between 4 and 5 to increase the stability of the extract. After clarification and dilution, the filtrate is then filter-sterilized with 0.2 µm filter porosity under sterile condition.

Example 5: Evaluation of the White Truffle on Skin Aging by Extracellular Matrix Evaluation on Fibroblasts The purpose of this study is to show the effect of the White Truffle extract on aging by the extracellular matrix (ECM) evaluation, regarding collagen I expression.

Protocol:

Normal human fibroblasts were treated twice a day for 48 hours with a solution of White Truffle extract, according to example 1, 2, 3 or 4, diluted at ¹⁄₂₀₀ eme in the culture medium, leading to a final concentration of 0.5% vol/vol.

For immunolabelling by anti-collagen I antibody, the cells were washed and fixed with cold methanol. The cells were then incubated in the presence of a specific anti-collagen I antibody (Tebu, ref. 600-401-103-0.5, rabbit polyclonal), and then a secondary suitable antibody, coupled with a fluorescent dye. After mounting in a particular medium, the slides were observed by epifluorescence microscope (Zeiss Axiovert 200M microscope). Fluorescence intensity was quantified by analyzing the image using Volocity® 6.3. software (PerkinElmer, Inc.).

Results:

Only the treatments with the White Truffle extract according to example 1 diluted at 0.5% for 48 hours showed a highly significant increase (Student's t-test) in collagen I expression on fibroblasts. The other extract application didn't show any efficacy.

The results are illustrated in FIG. 1.

Conclusions:

White Truffle extract at 0.5%, through the stimulation of collagen I, improved the extracellular matrix on fibroblasts. The extract according to example 1 gave the best results.

Example 6: Evaluation of the White Truffle Extracts on Lightening, by Melanin Content Evaluation on Ex Vivo Skin Biopsies The purpose of this study is to show the effect of the White Truffle extract on lightening by melanin content evaluation using Fontana-Masson staining. The Fontana-Masson staining is based on the melanin ability to reduce solutions of ammoniacal silver nitrate to metallic silver (brown) without the use of an external reducing agent.

Protocol:

Normal human skin biopsies of 6 mm of diameter were maintained ex vivo in a specific culture medium (DMEM at 1 g/L, HAMF12, fetal calf serum and antibiotics). Biopsies were treated twice a day for 48 hours with a solution of White Truffle extract, according to example 1, 2, 3 or 4 diluted at 1/200 eme in PBS, leading to a final concentration of 0.5% vol/vol, respectively. The control condition is performed by applying PBS 1x.

For Fontana-Masson staining, tissues were fixed and embedded in paraffin. Embedded skin biopsies were then cut and sections were deparaffinized and rehydrated. Then, a stock solution containing ammonium hydroxide and silver nitrate was added on each section. After a distilled water wash, biopsies were incubated with 5% sodium thiosulfate and washed again. After mounting in a particular medium, the slides were examined using an Eclipse E600 microscope (Nikon). The number of brown/dark pixels was quantified by analyzing the image using ImageJ software.

Results:

The treatments with the White Truffle extract according to examples 1 and 4 diluted at 0.5% for 48 hours showed a significant decrease (Student's t-test) of melanin content on ex vivo skin biopsies. The other extract application didn't show any efficacy.

Figure 2:
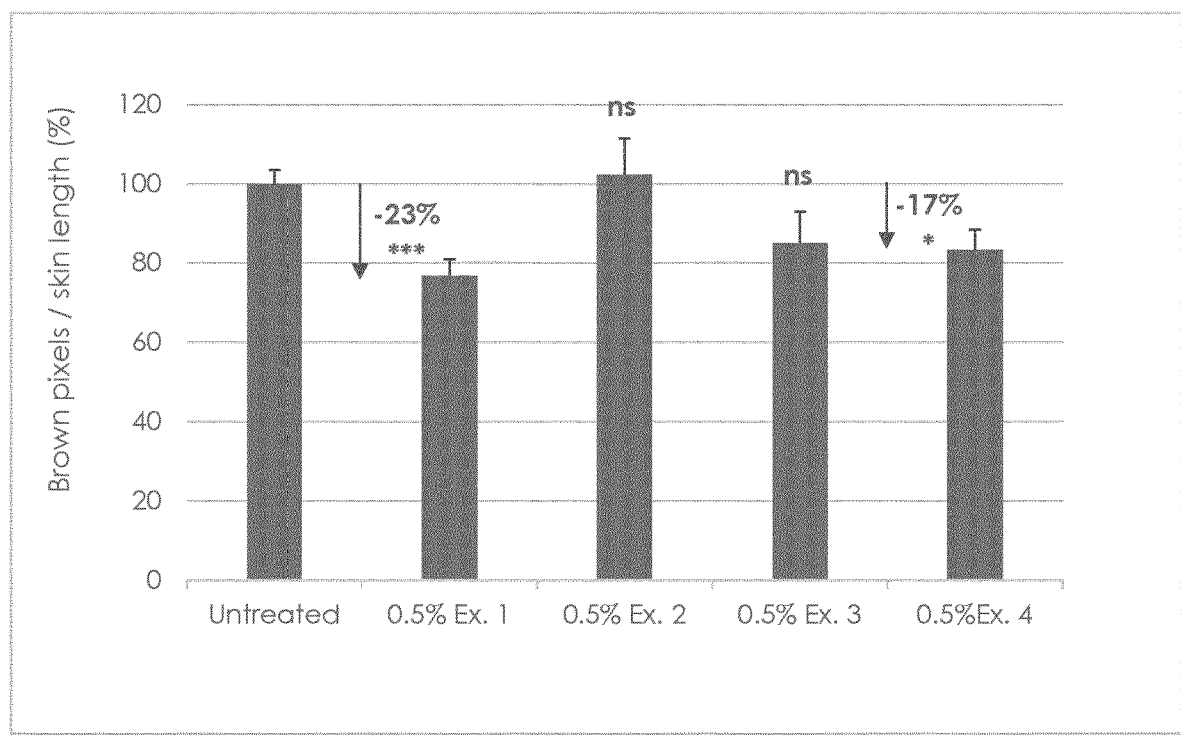
FIG. 2 is illustration of melanin content on ex vivo skin biopsies (Fontana-Masson).
Figure 3:
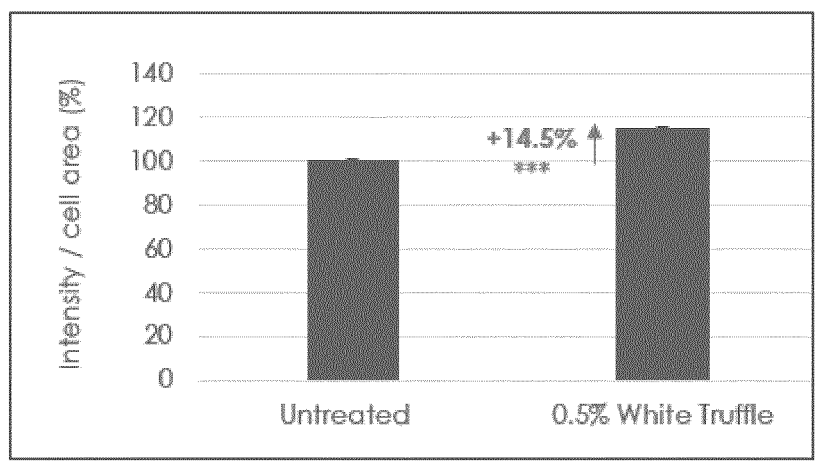
FIG. 3 is illustration of stimulation of LC3 (autophagy pathway), evaluated on keratinocytes.
Figure 4:
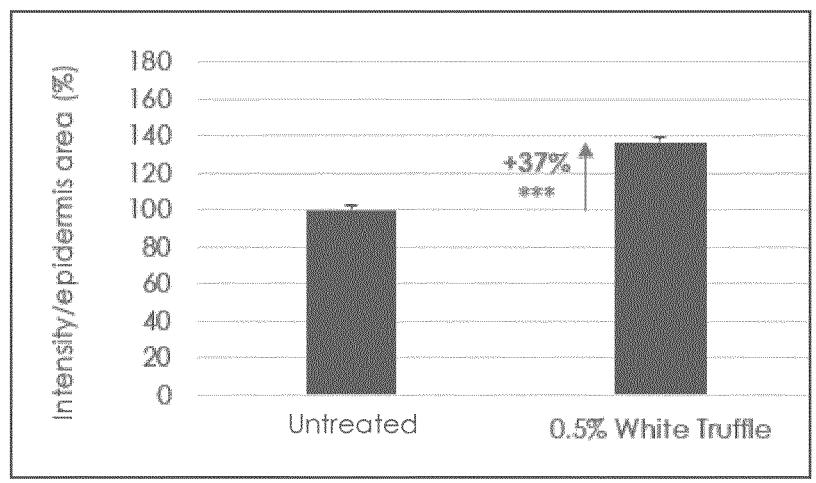
FIG. 4 is illustration of stimulation of LC3 (autophagy pathway), evaluated on ex vivo skin biopsies.

The results are illustrated in FIG. 2. It was observed that the extract according to ex. 1 gave better results than the extract according to ex. 4.

Conclusions:

White Truffle extract application at 0.5% showed a lightening efficacy by decreasing melanin content on ex vivo skin biopsies. The extract according to example 1 gave the best results.

The extract prepared according to example 1 was the only to act on both extracellular matrix and lightening pathways. It was selected as the best candidate.

Example 7: Evaluation of the White Truffle Extract According to Example Ion Autophagy Pathway, on Keratinocytes and Ex Vivo Skin Biopsies The purpose of this study is to show the effect of the White Truffle extract on autophagy. Autophagy is a catabolic process for the autophagosomic-lysosomal degradation of bulk cytoplasmic contents (Cuervo A M et al. "Autophagy, nutrition and immunology", Mol Aspects Med. 33(1):2-13, 2012). Here, LC3 (Microtubule-associated protein 1A/1B-light chain 3) which is a structural protein implicated in the formation of the autophagosomes (Melendez A and Levine B. "Autophagy in *C. elegans*", WormBook. 24:1-26, 2009) was evaluated.

Protocol:

Evaluation on Keratinocytes

Normal human keratinocytes were treated twice a day for 48 hours with a solution of White Truffle extract, according to example 1, diluted at 1/200 eme in the culture medium, leading to a final concentration of 0.5% vol/vol.

For immunolabelling by LC3 antibody, the cells were washed and fixed with cold methanol. The cells were then incubated in the presence of a specific LC3 antibody (Cell Signaling, ref. PM036, rabbit polyclonal), and then a secondary suitable antibody, coupled with a fluorescent dye. After mounting in a particular medium, the slides were observed by epifluorescence microscope (Zeiss Axiovert 200M microscope). Fluorescence intensity was quantified by analyzing the image using Volocity® 6.3. software (PerkinElmer, Inc.).

Evaluation on Ex Vivo Skin Biopsies

Normal human skin biopsies of 6 mm of diameter were maintained ex vivo in a specific culture medium (DMEM at 1 g/L, HAMF12, fetal calf serum and antibiotics). Biopsies were treated twice a day for 48 hours with a solution of White Truffle extract, according to example 1, diluted at 1/200 eme in PBS, leading to a final concentration of 0.5% vol/vol, respectively. The control condition is performed by applying PBS IX.

For immunolabelling by LC3 antibody, tissues were fixed and embedded in paraffin. Embedded skin biopsies were then cut and sections were deparaffinized and rehydrated. Then, an unmasking protocol was performed before applying a specific anti-LC3 antibody (Cell Signaling, PM036, rabbit polyclonal), and then a secondary suitable antibody, coupled with a fluorescent dye. After mounting in a particular medium, the slides were observed by epifluorescence microscope (Zeiss Axiovert 200M microscope).

Results:

The treatments with a solution of White Truffle extract diluted at 0.5% for 48 hours showed a highly significant increase (Student's t-test) in LC3 expression both on keratinocytes and ex vivo skin biopsies.

Conclusion:

White Truffle extract at 0.5%, through the stimulation of LC3, improved the autophagy pathway.

The invention claimed is:

1. A cosmetic composition in the form of an oil-in-water emulsion, water-in-oil emulsion or multiple emulsion, consisting essentially of a butylene glycol/1,2 hexanediol extract of *Tuber magnatum* obtained by a process of:

(a) grinding *Tuber magnatum*;

(b) adding water to the grounded *Tuber magnatum* to make a mixture,
(c) agitating the mixture by maintaining the temperature from 25° C. to 50° C.,
(d) filtering the mixture to remove any solid parts of the *Tuber magnatum* to obtain a *Tuber magnatum* extract; and
(e) diluting the *Tuber magnatum* extract in a mixture of 30% butylene glycol and 2% 1,2 hexanediol to obtain the oil-in-water emulsion, water-in-oil emulsion or multiple emulsion, butylene glycol/1,2 hexanediol extract of *Tuber magnatum*;
wherein the *Tuber magnatum* extract consists essentially of compounds having a molecular weight of less than 60 kDa;
consists essentially of from 0.5 to 1.5 g/kg of dry matter, from 0.05 to 0.15 g/kg of protein, from 0.35 to 1.05 g/kg of sugar, from 0.025 to 0.075 g/kg of amino acids; and from 0.05 to 0.15 g/kg of phenolic compounds.

* * * * *